United States Patent [19]
Watson et al.

[11] Patent Number: 5,964,096
[45] Date of Patent: Oct. 12, 1999

[54] METHOD AND PACKAGE DESIGN FOR CRYOPRESERVATION AND STORAGE OF CULTURED TISSUE EQUIVALENTS

[75] Inventors: Stephen R. Watson; Mehmet Toner; Alexander G. Tschumakow, all of Canton, Mass.

[73] Assignee: Organogenesis Inc., Canton, Mass.

[21] Appl. No.: 08/913,021

[22] PCT Filed: Jan. 30, 1996

[86] PCT No.: PCT/US96/01217

§ 371 Date: Jul. 30, 1997

§ 102(e) Date: Jul. 30, 1997

[87] PCT Pub. No.: WO96/24018

PCT Pub. Date: Aug. 8, 1996

[51] Int. Cl.[6] .................................................. C12M 3/00
[52] U.S. Cl. ............................................. 62/78; 435/297.5
[58] Field of Search ....................... 62/78, 60; 435/289.1, 435/297.1, 305.4, 297.5

[56] References Cited

U.S. PATENT DOCUMENTS

| | | | |
|---|---|---|---|
| 2,348,448 | 5/1944 | Brewer | 435/297.1 X |
| 2,533,088 | 12/1950 | Brewer et al. | 435/297.1 X |
| 3,203,870 | 8/1965 | Andelin | 435/297.1 X |
| 3,248,302 | 4/1966 | Mackin | 435/297.1 X |
| 4,670,398 | 6/1987 | Song | 435/297.1 X |
| 4,871,674 | 10/1989 | Matsui et al. . | |
| 4,912,037 | 3/1990 | Lemonnier | 435/297.1 X |
| 4,988,302 | 1/1991 | Smith et al. | 435/297.1 |
| 5,034,331 | 7/1991 | Brewer | 435/297.1 X |
| 5,272,083 | 12/1993 | Butz et al. | 435/297.1 X |
| 5,358,871 | 10/1994 | Stevens et al. . | |
| 5,366,893 | 11/1994 | Stevens et al. . | |
| 5,466,602 | 11/1995 | Lyman et al. . | |
| 5,470,743 | 11/1995 | Mussi et al. | 435/297.1 |
| 5,534,227 | 7/1996 | Lahm et al. | 435/305.4 X |
| 5,795,775 | 8/1998 | Lahm et al. | 435/305.4 X |
| 5,830,746 | 11/1998 | Copeland et al. | 435/305.4 X |

*Primary Examiner*—Christopher B. Kilner
*Attorney, Agent, or Firm*—Hale and Dorr LLP

[57] ABSTRACT

This invention is directed to an efficient cryopreservation package desgin of harvested mammalian tissues and living cultured tissue equivalents made by in vitro technology. The invention involves immersing a mammalian tissue or cultured tissue equivalent in a cryoprotectant solution, agitating the cryoprotectant solution and the immersed tissue to achieve effective penetration of the cryoprotectant solution into the tissue, and then freezing the tissue at a very slow freezing rate. In the freezing step, extracellular ice formation is initiated by seeding. The cryopreserved tissue may be stored for indefinite periods of time prior to use. The cultured tissue equivalent is an in vitro model of the equivalent human tissue, such as skin or cornea, which, when retrieved from storage can be used for transplantation or implantation in vivo or for screening compounds in vitro.

20 Claims, 7 Drawing Sheets

METHOD AND PACKAGE DESIGN FOR CRYOPRESERVATION AND STORAGE OF CULTURED TISSUE EQUIVALENTS

BACKGROUND OF THE INVENTION

1. Field of the Invention

This invention relates to the cryopreservation of both harvested tissue and cultured tissue equivalents made using in vitro technology. This invention also relates to a cryopreservation package design for both harvested tissue and cultured tissue equivalents that is both a cost effective and easy to handle package design that allows for maximal viability of the tissue or tissue equivalent to be cryopreserved. By use of the cryopreservation technology, either cryopreserved harvested tissue or cryopreserved cultured tissue may be stored for indefinite periods of time prior to use. The cultured tissue is an in vitro model of the equivalent human tissue, which, when retrieved from storage, can be used for transplantation or implantation, in vivo, or for screening compounds in vitro.

2. Brief Description of the Background of the Invention

In vitro technology has developed tissue equivalents for the purposes of in vitro testing or in vivo grafting for wound repair. Methods of producing such tissue equivalents are disclosed in U.S. Pat. Nos. 4,485,096, 4,604,346, 4,835,102 and 5,374,515 and U.S. Ser. Nos. 08/193,809 and 08/337,830; all of which are incorporated herein by reference.

The shelf life of living tissues is limited and, subsequently, their window of use is short, resulting in much waste. There is a need to preserve such tissues for extended periods of time, as for shipping and storage, until their use. Both the development of a cryopreservation method and a package for cryopreservation and storage would extend the window of use indefinitely, ease shipping and allow for the maintenance of an inventory. To enable an inventory of tissue at burn care centers and hospitals is also desirable. Other advantages are that samples can be retained from different stages of the manufacturing cycle for quality control archives and larger production batches can be made as they can be maintained in a frozen state.

Currently, the storage time of cellular biological materials is extended by cooling to "cryogenic" temperatures. The transition from the liquid into the solid state by lowering the temperature of the system can take place either as crystallization (ice), involving an orderly arrangement of water molecules, or as vitrification or amorphization (glass formation), in the absence of such an orderly arrangement of crystalline phase. The challenge for a cryobiologist is to bring cells to cryogenic temperatures and then return them to physiological conditions without injuring them.

There are two basic approaches to cryopreservation of cells and tissues: freeze-thaw and vitrification. In freeze-thaw techniques, the extracellular solution is frozen (i.e., in crystalline form), but steps are taken to minimize the intracellular ice formation. In vitrification procedures, there is an attempt to prevent ice formation throughout the entire sample. The former approach is problematic in that if ice crystals are formed inside the cells, they are detrimental to cell viability upon thawing. However, cells could survive a freeze-thaw cycle if they are cooled at controlled rates in the presence of non-toxic levels of cryoprotectants. The latter approach of vitrification seeks to avoid potentially damaging affects of intra- and extracellular ice by depressing ice formation using very high concentrations of solutes and/or polymers. However, the cell damage may occur to long exposure to toxic levels of these additives required for vitrification.

Cryoprotectants protect living cells from the stresses involved in the freezing process. One way cryoprotectants protect cells is by diluting the salt that becomes increasingly concentrated in the unfrozen solution as water is transformed to ice. The amount of ice is dictated by the temperature and initial composition of the solution; whereas the amount of unfrozen fraction is a function of temperature only. Cryoprotectants have several other functions. An important one is that they usually reduce the intracellular ice formation temperatures. Another function is that they stabilize membranes and proteins.

All solutions will supercool below their freezing point until they find a random nucleation site for crystal formation. When cryopreserving by a freeze-thaw method, ice formation in the extracellular medium should be deliberately initiated by seeding at low degrees of supercooling. If ice formation is not induced by seeding, ice will form spontaneously when the solution is cooled sufficiently far below its equilibrium freezing point. Because this process is random in nature, ice formation will occur at random, unpredictable temperatures; consequently, survival rates will be highly variable between repeated trials with the same freezing protocol. Furthermore, the extremely rapid crystallization which results when ice forms in a highly supercooled solution can cause damage to cells and tissues. Moreover, it has been shown that if extracellular ice formation is initiated at high degrees of supercooling, the probability of intracellular ice formation is drastically increased. This phenomenon results from the delayed onset of freeze-induced cell dehydration, which results in increased retention of intracellular water, and thus higher likelihood of ice formation in the cell.

Once the extracellular ice is seeded and the sample is surrounded by the ice phase, it is necessary to cool the sample to a cryopreserved state. The cooling step is one of the most critical steps in a freeze-thaw protocol. Due to the formation of ice, i.e., pure water, the partially frozen extracellular solution is more concentrated than the intracellular compartment. As a consequence, the cell will dehydrate by losing water in an attempt to restore thermodynamic equilibrium. As the system cools, more extracellular ice is generated and the concentration of solutes rises and forces the cells to dehydrate further. There are three characteristics of the cells that control their rate of dehydration. One is the cell membrane water permeability; the lower the water permeability, the longer it takes for the cells to dehydrate. Another is the temperature dependence of the cell membrane water permeability; all cells decrease their water permeability with decreasing temperatures. The final is cell size; larger cells take longer to dehydrate than smaller cells. Given that each cell type may have drastically different characteristics, the optimal cryopreservation conditions can vary by orders of magnitude for different cell types.

Although the exact mechanisms of cell damage during cryopreservation has not yet been completely elucidated, characteristic survival signatures generated by measuring cell survival as a function of cooling rate appear to be qualitatively similar for all cell types and displays an inverted U-shaped curve. Cell survival is low at very slow and very fast cooling rates, and there is an intermediate cooling rate yielding optimal survival. Even though the optimal cooling rate and the width of the curve can vary drastically for different cell types, the qualitative behavior appears to be universal. Faster cooling rates do not allow cells enough time to dehydrate and cells form ice internally. Cell injury at fast cooling rates is attributed to intracellular ice formation. At slow rates of cooling, cell injury is thought to be due to the effects of exposure to highly concentrated intra- and extracellular salt and cryoprotectant solutions or to the mechanical interactions between cells and the extracellular ice.

It is necessary to dehydrate the cells as much as possible before they cross the intracellular ice nucleation curve. It is at this point that practically all water remaining in the cell will nucleate and form ice. It is impractical to determine the exact temperature where this will happen but it is approximately −40° C. to −50° C. when the cells are slowly frozen in the presence of 1M to 2M concentrations of cryoprotectants. It is important to note that the amount of water that turns to ice inside a cell at this point may be innocuous when frozen, but if not thawed fast enough, it will expand and kill the cell upon thawing. (*The Biophysics of Organ Cryopreservation,* Pg. 117–140, edited by David E. Pegg and Armand M. Karow, Jr. NATO ASI Series A: Life Sciences Vol. 147 1987 Plenum Press, New York 233 Spring St., New York, N.Y. 10013).

Before the development of a commercially viable skin equivalent, cadaver skin was used for the purposes of grafting. Cryopreservation protocols were developed so that burn centers and hospitals could maintain skin banks. A number of different protocols were developed utilizing different cryoprotectants, freeze rates, packaging formats and storage conditions. Most researchers agreed upon a fast thaw protocol. The success or failure of the protocol was measured either by graft take to a wound bed or by cell viability assay.

In U.S. Pat. No. 3,842,831 to Beisang is disclosed a method for the cryopreservation of cadaver skin patches. The method involves the attachment of the cadaver skin to a loosely woven scrim or backing and, together, the skin patches and the scrim are rolled prior to freezing. No cryoprotectant is employed, though the inventors suggest the use of either glycerin or DMSO. The freezing protocol employs a fast uncontrolled (fixed temperature) freeze rate protocol to a cryogenic temperature of −70° C.

May SR and FA DeClement (*Skin Banking Methodology,* 17, 33–45 (1980)) performed an evaluation of packaging geometry and cooling and warming rates using dermatome cadaver skin. The results suggested that cadaver skin be flat, rather than rolled, and that a slower controlled rate of freezing be employed.

U.S. Pat. No. 5,040,677 to Tubo discloses a gas-tight sealable container for individual grafts of epithelial cell sheets. The container requires that the epithelial cell sheet be attached to an adhesive substrate sheet or backing by use of clips.

U.S. Pat. No. 5,145,770 to Tubo discloses a cryopreservation method for keratinocyte sheets that employs a cryoprotectant of a non-cell penetrating agent, such as dextran, and a cell penetrating reagent, such as glycerol, with a cooling rate of about −1° C./minute. Similarly, EP 0 364 306 to Chao et al, discloses a method for cryopreserving a sheet of living, cultured epithelial cells but utilizing both DMSO and glycerol as a cryoprotectant and a freezing protocol of preferably −1° C./minute.

U.S. Pat. No. 5,298,417 to Cancedda et al, discloses a cryopreservation protocol developed for single layer constructs such as epithelial sheets prepared as described in U.S. Pat. Nos. 4,016,036, 4,304,866 and 4,456,687. Epidermal sheets were incubated with a cryoprotectant of either 8–15% glycerol or DMSO and were cryopreserved by employing a controlled rate protocol where the cooling rate is slower at the start than at the end of the protocol and is characterized by an increase in temperature before the culmination of the freezing procedure.

A method for the cryoprotection of dermal fibroblasts in a collagen gel was investigated by Teasdale et al, *Burns,* 19 (5) 406–410 (1993). Teasdale determined that optimum cell viability could be obtained by freezing at −0.5° C./minute with DMSO as a cryoprotectant.

Nanchahal et al., "Cultured composite skin grafts: Biological skin equivalents permitting massive expansion," *The Lancet,* 2 (8565), 191–193 Jul. 22, 1989), discusses a technique for storage of composite cultured tissue grafts utilizing a cryoprotectant of 15% glycerol and 10% FCS in Medium 199. The grafts and the cryoprotectant, were incubated at 37° C. for two hours and were then frozen at −1° C. per minute to −70° C. and then stored in liquid nitrogen. After fast thawing of the grafts, their viability was determined by culturing for two weeks and by grafting to hairless mice. A final evaluation was made by grafting to three patients undergoing tattoo excision.

Johnstone et al. "Cryopreservation of Rabbit and Cat Corneas at −18 to −24° C.," *Cornea,* 11(3): 211–220 (1992), is directed to a simple procedure for cryopreservation of rabbit and cat corneas which utilizes a domestic freezer rather than liquid nitrogen or very low temperature freezers. Perfusion of cryopreservative is obtained by placing corneas in successive solutions of 50% fetal calf serum and McCarey-Kaufman medium with increasing glycerol and glucose content.

Using prior art methods, it is not possible to cryopreserve cultured tissue equivalents, in part because they are relatively thick and of heterogeneous cell layers. One of the functions of these tissues in vivo are to provide a permeability barrier. Tissue functions have to be considered in the development of a cryopreservation protocol.

The present inventors have discovered a method for cryopreservation and, in particular, a package design, that is applicable to a number of cultured tissue equivalents and to mammalian skin, one that is a surprisingly effective and commercially practical package for the cryopreservation of cultured tissue equivalents.

SUMMARY OF THE INVENTION

The present invention provides a method for the successful cryopreservation of cultured tissue equivalents at very low temperatures which avoids the formation of harmful intracellular ice crystals, minimizes the effective concentration of potentially harmful chemicals, and permits the rapid introduction and removal of cryoprotectants at feasible temperatures using programmable freezing equipment.

The present invention also provides a new package design developed for the cryopreservation, storage and distribution of cultured tissue equivalents. The new design offers many advantages over existing package designs. At present, there are no commercially available cryopreserved cultured tissue equivalents, therefore there are no off-the-shelf package designs available. The design of the new package enables better temperature tracking of the package interior with the exterior temperature of the freezing chamber because of more efficient heat transfer. An improved heat transfer rate allows for a more controlled process; thus, uniform cooling and warming rates of the cultured tissue equivalent, thereby reducing variability in cell viability.

The inventors have discovered a method for cryopreserving cultured tissue equivalents made from in vitro techniques so that the tissues maintain their viability and utility as equivalents of human tissues. The invention includes the use of agitation to enhance the penetration of an effective amount of cryoprotectant. The present method provides for the cryopreservation of both harvested tissue and cultured tissue equivalents in a manner which protects structural integrity and cellular viability.

The method of this invention involves the following steps:

1) The harvested tissue or cultured tissue equivalent is immersed in a cryoprotectant solution and the cryoprotectant solution and the immersed tissue are agitated to achieve effective penetration of the cryoprotectant solution into the tissue (perfusion of the tissue); and, 2) After the perfusion of the cryoprotectant solution into the tissue, cooling to solid-liquid phase equilibrium temperature range for the cryoprotectant; seeding extracellular ice and cooling to a cryopreserved state by freezing the tissue at a slow freezing rate to a temperature at or below at least about $-70°$ C., more preferably at or below $-120°$ C., even more preferably at $-140°$ C. and most preferably, at $-196°$ C.

Once frozen, the cryopreserved tissue can be stored for indefinite time periods between temperatures of about $-120°$ to about $-196°$ C., the temperature of liquid nitrogen.

Thawing the cryopreserved tissue is accomplished by warming the frozen tissue at a high rate, which is done in about 1 to 2 minutes. The frozen tissue may be thawed by direct application of warmed culture media or by physiologic buffered solution or by another rapid heating method. The package design allows for thawing of the tissue by immersion of the package in a waterbath as the package design ensures both a fast warming rate and controlled thermal uniformity while maintaining sterility during he critical thawing procedure.

Prior to use as an equivalent for human tissue, for grafting or in vitro testing, the thawed cultured tissue equivalent is rinsed to remove the cryoprotectant solution. The cryoprotectant solution may be removed by rinsing with, for example, an isotonic buffer solution at physiological pH. The cultured tissue equivalents can then be stored temporarily in such a buffer solution or recultured in an appropriate cell medium before use.

DETAILED DESCRIPTION OF THE INVENTION

Tissue engineering is an emerging area which utilizes cultured tissue cells to construct tissue equivalents which can be used to examine the response to injury by chemical agents or pharmaceutical compounds. The cultured tissue may also be used to form graftable human tissue.

Tissue equivalents have been described extensively in many patents, including U.S. Pat. Nos. 4,485,096; 4,485,097; 4,539,716; 4,546,500; 4,604,346; 4,837,379; and 5,374,515, all of which are incorporated herein by reference. One successful application of the tissue equivalent is called the "Living Skin Equivalent," which has a morphology similar to actual human skin. The Living Skin Equivalent (LSE) is composed of two layers: the upper portion is made of differentiated and stratified human epidermal keratinocytes that cover a lower layer of human dermal fibroblasts in a collagen matrix. Parenteau, et al., "Epidermis Generated In Vitro: Practical Considerations and Applications," *J. of Cellular Biochemistry,* 45:245–251 (1991); Parenteau, et al., "The organotypic culture of human skin keratinocytes and fibroblasts to achieve form and function," *Cytotechnology,* 9:163–171 (1992); and Bell et al., "The Living Skin Equivalent: Its Manufacture, Its Organotypic Properties and Its Responses to Irritants," *Toxic. in Vitro,* 5:591–596 (1991). LSE for grafting is under investigation in clinical trials for indications relating to partial and full thickness skin wounds: excision surgery, burns, venous stasis ulcers, diabetic ulcers, decubitus ulcers, and chronic inflammatory ulcers. The LSE is a full-thickness, bilayered, in vitro engineered skin tissue.

An in vitro organ equivalent of the cornea of the eye has been developed as described in U.S. Pat. No. 5,374,515, incorporated herein by reference. The cornea tissue equivalent has three distinct cell layers, the external layer, a stratified squamous epithelium; the middle layer of collagen fibers and stromal cells; and an inner layer, simple squamous epithelium, also called the corneal endothelium. An in vitro cornea equivalent can be used for in vitro toxicity assays to serve as accurate and inexpensive non-animal predictive models of in vivo ocular and dermal irritation potential for many types of products and raw materials.

The goal of cryopreservation is to preserve the structural integrity and viability of biological materials for an indefinite period of time so that these materials can be available and used as needed. Complex tissues of finite life span will require cryopreservation to expand product availability and utility. The history of cryopreservation of biological material, however, has shown that the optimization of a cryopreservation protocol for a particular cell does not necessarily give good results when used with another cell type or with other cells in a tissue. The development of more specialized methods due to the differences in cell density, water content and level of structural organization of the full-thickness tissue equivalents was required. The cryopreservation protocols of this invention are surprisingly applicable to the single layer epidermal and dermal layers alone, bilayer tissue equivalents, trilayered cornea equivalents and harvested mammalian skin. The development of a package design makes cryopreservation of these tissues practical for production scale processes.

As used herein, the term "cultured tissue equivalents" means tissue equivalents of mammalian tissues, wherein the tissue equivalents are made by in vitro techniques and are meant to include monolayer skin equivalents, either a dermal equivalent or an epidermal sheet; bilayered skin equivalents, particularly LSE; and trilayered cornea equivalents and skin equivalents. The morphology of the cultured tissue equivalents are similar to the in vivo mammalian organ, typically the human organ. For illustration, the morphology of the LSE bears many similarities to human skin. Metabolically and mitotically active human dermal fibroblasts (HDF) are found throughout the dermal layer of the construct, and have been shown to secrete collagen and other matrix components into the lattice. The epidermis consists of a basal layer shown to divide with a mitotic rate similar to that of human skin. The suprabasal epidermis shows the same strata as skin in vivo, with well defined spinous and granular layers containing keratohyalin and lamellar granules covered by a stratum corneum. Immunohistochemistry demonstrates the presence of extracellular matrix components routinely found at the dermo-epidermal junction in normal human skin, such as laminin, Type IV collagen and kalanin (GB3).

Cultured tissue equivalents obtained by organotypic culture methods, such as the Living Skin Equivalent (LSE), utilize a carrier as a framework on which to form the equivalents. Cultured tissue equivalents are fabricated on a carrier which allows for the manipulation of the construct during manufacturing, shipping and end use without directly contacting the construct. Methods for producing cultured tissue equivalents on a carrier are disclosed in U.S. Pat. No. 5,374,515 and U.S. Ser. Nos. 08/193,809 and 08/337,830.

A carrier includes a flat permeable membrane which is attached to one end of an essentially tubular support. The other end of the tubular support includes an outwardly extending flange which in turns carries a rim that can hang upon the upper end of a well in a tissue culture dish and in the package design of the present invention. The membrane-support assembly is sized to be used with a culture dish having at least one well of a specific size so as to provide the proper clearance about the support and engage the top end of the well. The membrane-support assembly may be made in different sizes so as to be used with different sizes of both culture dishes and cryopreservation and storage packages. Examples of these carriers is a TRANSWELL® (Costar) as described in U.S. Pat. No. 5,466,602. Modifications to the package design may be made by the skilled artisan to accommodate similar carriers that employ different means of support and engagement in the culture vessels. Similar carriers are described in U.S. Pat. Nos. 5,358,871 and 5,366,893 or those described in U.S. Pat. No. 4,871,674.

The preferred package design of this invention incorporates the carrier framework and defines an environment around the tissue equivalent that is able to be controlled to predetermined specifications. The present invention uses materials that are preferably of medical grade quality and are able to withstand a wide range of temperatures. These materials are molded to form a tray and a lid that are able to be sealed together by a sealing means. The new package is designed to incorporate a carrier support on which tissue equivalents are formed.

The new package design comprises a tray, a lid and a tight seal therebetween. The tray and the lid are designed to fit the existing carrier containing the attached tissue equivalent. The carrier with the attached tissue equivalent are placed into the tray and cryoprotectant solution is added. The lid is then placed onto the tray and the two parts are sealed together to form a tight seal between the interior and exterior environments of the package.

The package design allows for an equal distribution of cryoprotectant below the carrier and above the surface of the tissue equivalent while maintaining contact of cryoprotectant to the tissue equivalent and both the tray and the lid. The design of the package is based on the concept that controlled cooling and freezing rates can be maintained with an equal volume of cryoprotectant, arranged with a similar geometry above and below the cultured tissue to be cryopreserved. This arrangement provides a uniform distance, measured from both top and bottom surfaces of the cultured tissue equivalent to the exterior wall of the package (provided that the package also has uniform thickness). This uniformity should provide uniform heat exchange from the tissue equivalent to the freezing chamber upon cooling; and from the external environment to the tissue equivalent, upon thawing.

The tray comprises a bottom surface that is contiguous with a sidewall and a flange. The flange provides a planar surface for sealing of the tray to the lid. The sidewall of the tray has a singular continuous or a plurality of discontinuous supports inwardly extending from and integral with the sidewall. The upper edge of the carrier containing the cultured tissue equivalent, when positioned in the tray, is suspended on the supports provided by the sidewall of the tray. A space is defined between the suspended carrier and the bottom surface of the tray measuring about 1.0 mm in thickness with an area about the size of the tissue equivalent.

The lid comprises a planar bottom surface contiguous with a sidewall and a flange. The diameter of the lid flange is slightly smaller that the diameter of the tray flange. The lid flange, when placed on the tray containing a carrier, rests on the carrier so that the top surfaces of both the tray flange and the lid flange are in contact oriented on or about the same plane. A second space is defined by the lid and the surface of the cultured tissue equivalent also measuring about 1.0 mm in thickness with an area about the size of the tissue equivalent.

The design allows for a total of about 1 mm between the tray and bottom of the carrier containing the tissue equivalent disposed thereon and about 1 mm between the lid and tissue equivalent with the cryoprotectant above and below the tissue equivalent in contact with both the lid and tray. When the lid is placed in the tray containing medium, the lid displaces any air in the package to the peripheral space containing the tubular support of the carrier.

The lid is sealed to the tray along the exposed plane created by the top surfaces of the tray and lid flanges. Sealing may be accomplished by heat, adhesive or other means known in the art. The seal between the lid and the tray prevents leakage of cryoprotectant and maintains the sterility of the interior of the unit. Preferably an annular sheet of heat sealable lid stock is heat sealed to both the tray and lid flanges thereon. The lid stock preferably has a tab for peelably removing, and therefor unsealing, the lid from the tray to access the tissue equivalent. In another embodiment, a lid with a flange of about the same diameter as the tray flange is placed on a tray with a carrier disposed within so that the bottom surface of the lid flange intimately contacts the top surface of the tray flange. The flanges are then sealed together by a sealable means.

Figure 1A:
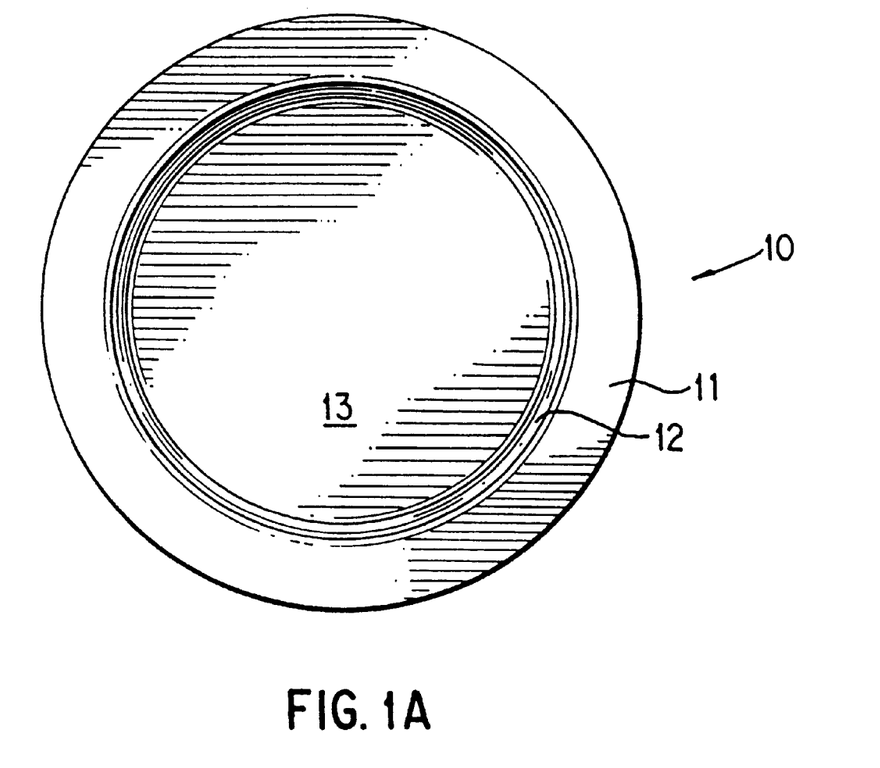
FIGS. 1A and 1B show views of the lid.
Figure 1B:
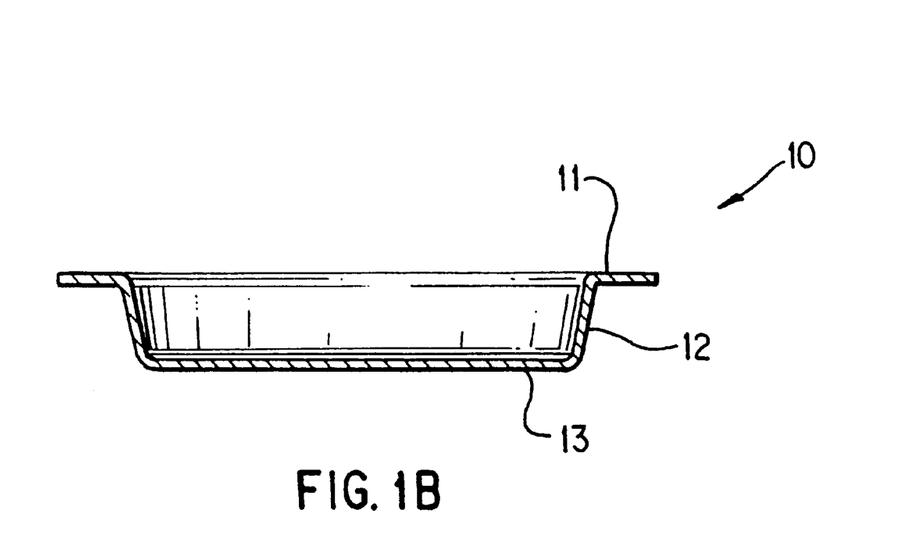

FIGS. 1A and 1B show the lid 10; lid flange 11; lid sidewall 12; and bottom surface 13. Lid flange 11, lid sidewall 12 and bottom surface 13 form a contiguous surface.

Figures 2, 3A:
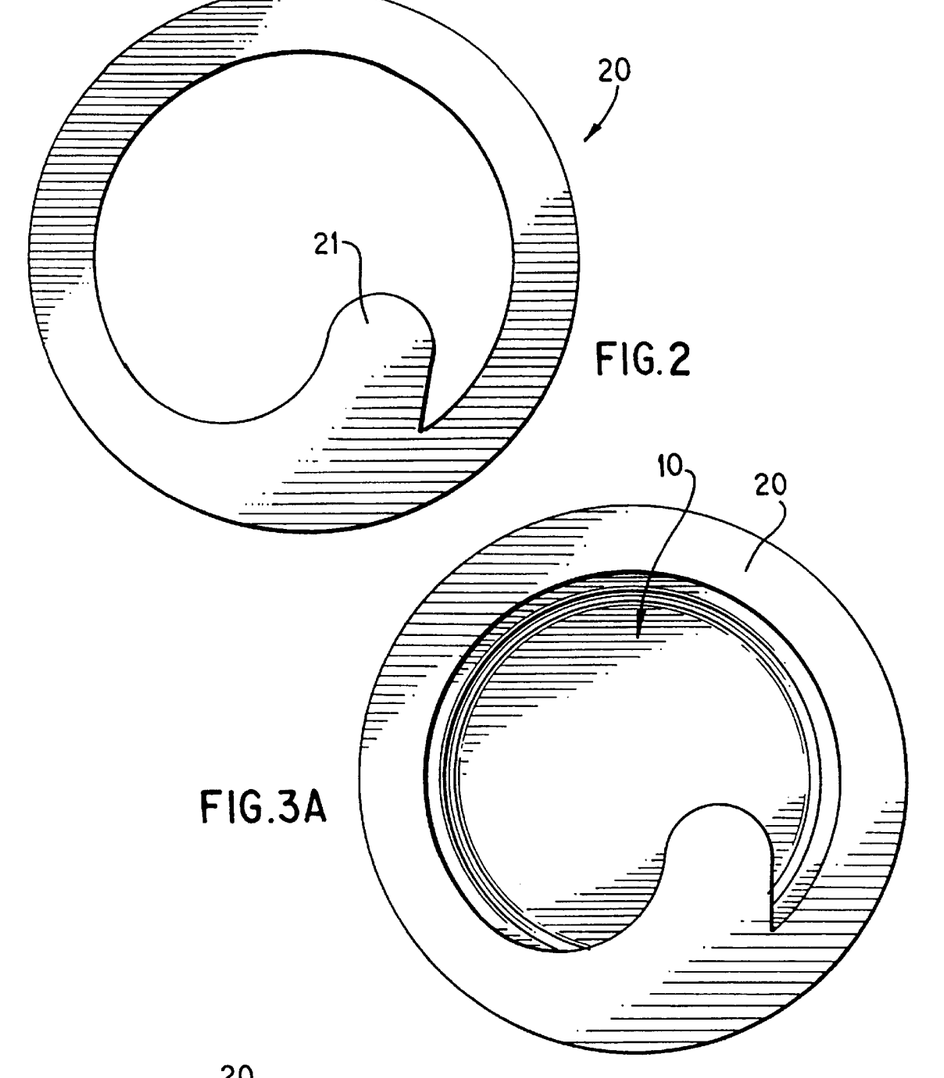
FIG. 2 shows a top view of the seal.
FIGS. 3A and 3B show views of the seal mounted to the lid.

FIG. 2 shows the annular seal 20 and pull 21.

Figure 3B:
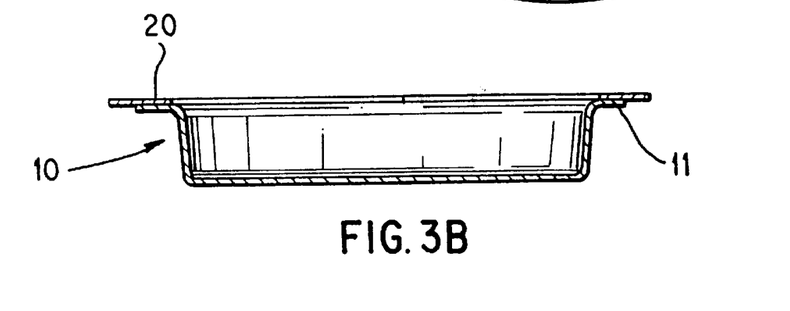

FIGS. 3A and 3B show the seal 20; lid 10; lid flange 11. Seal 20 is mounted to the lid flange 11 of the lid 10 prior to use to facilitate alignment of the seal during the sealing process.

Figure 4A:
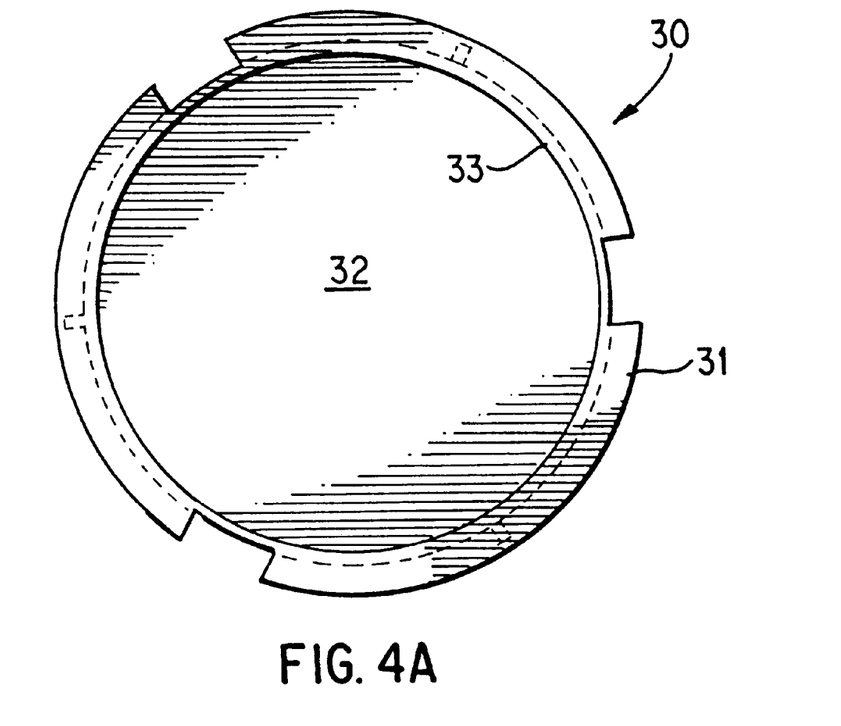
FIGS. 4A and 4B show views of the carrier.
Figure 4B:
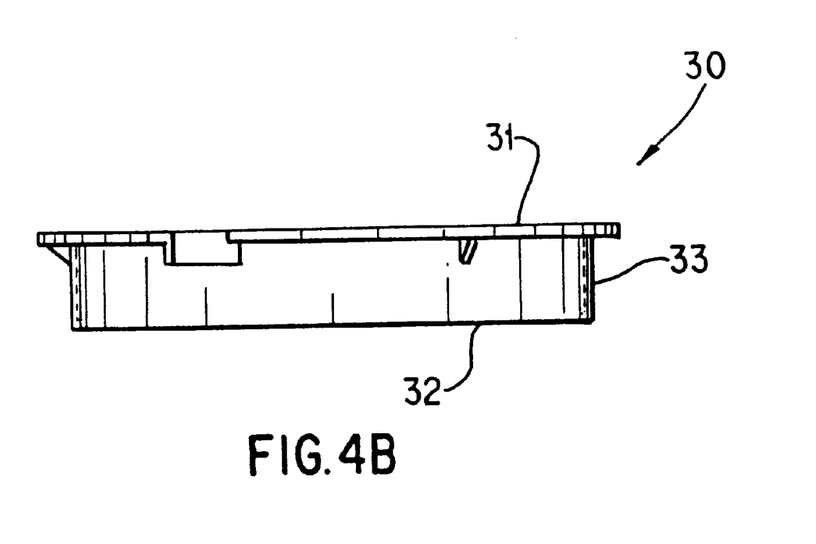

FIGS. 4A and 4B show the carrier 30; carrier rim 31; permeable membrane 32; and tubular support 33. The permeable membrane 32 contains a cultures tissue equivalent disposed thereon bound by the tubular support 33. The carrier 30 allows transfer of the tissue equivalent without contact or removal of the tissue equivalent throughout the cryopreservation process.

Figure 5A:
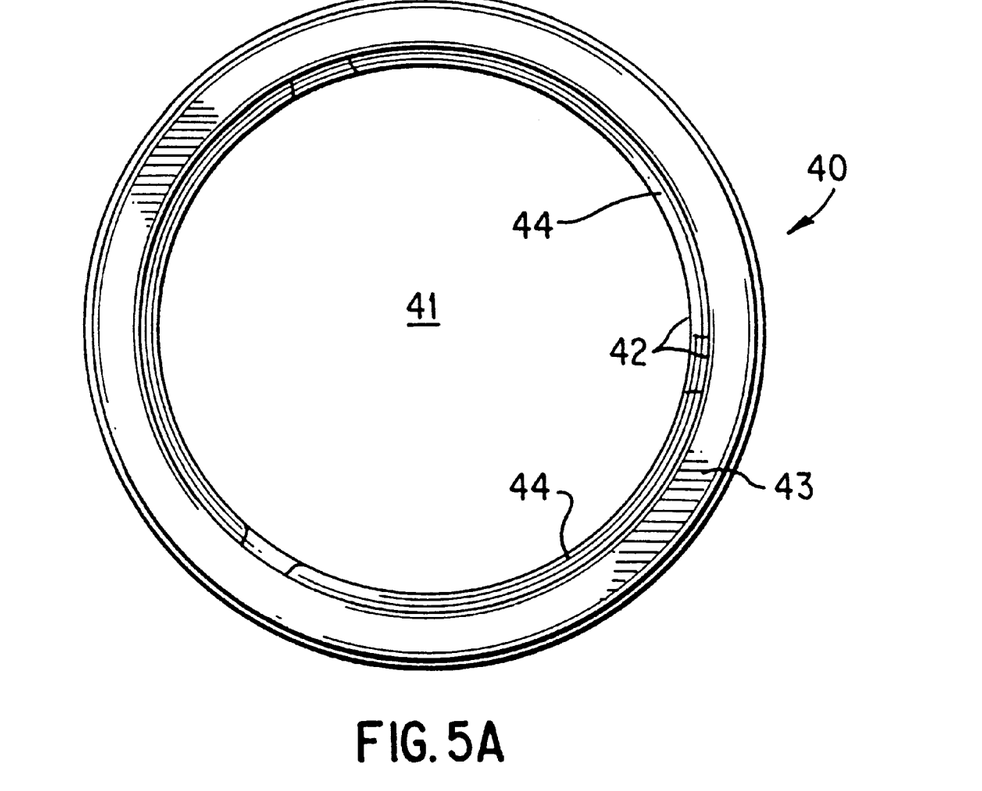
FIGS. 5A and 5B show views of the tray.
Figure 5B:
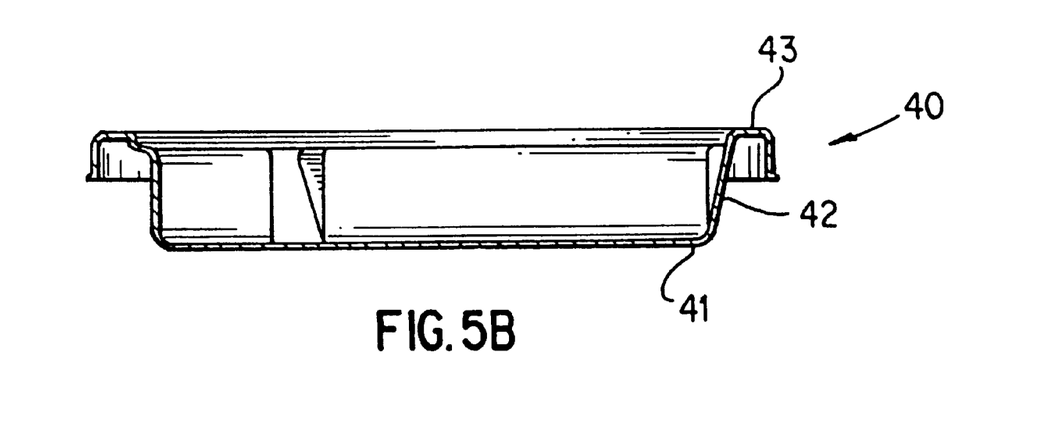

FIGS. 5A and 5B show tray 40; tray bottom surface 41; tray sidewall 42; tray flange 43; and carrier supports 44. The tray bottom surface 41, tray sidewall 42, tray flange 43, and carrier supports 44 form a contiguous surface. Carrier supports 44 contact and support the carrier within the tray.

Figure 6A:
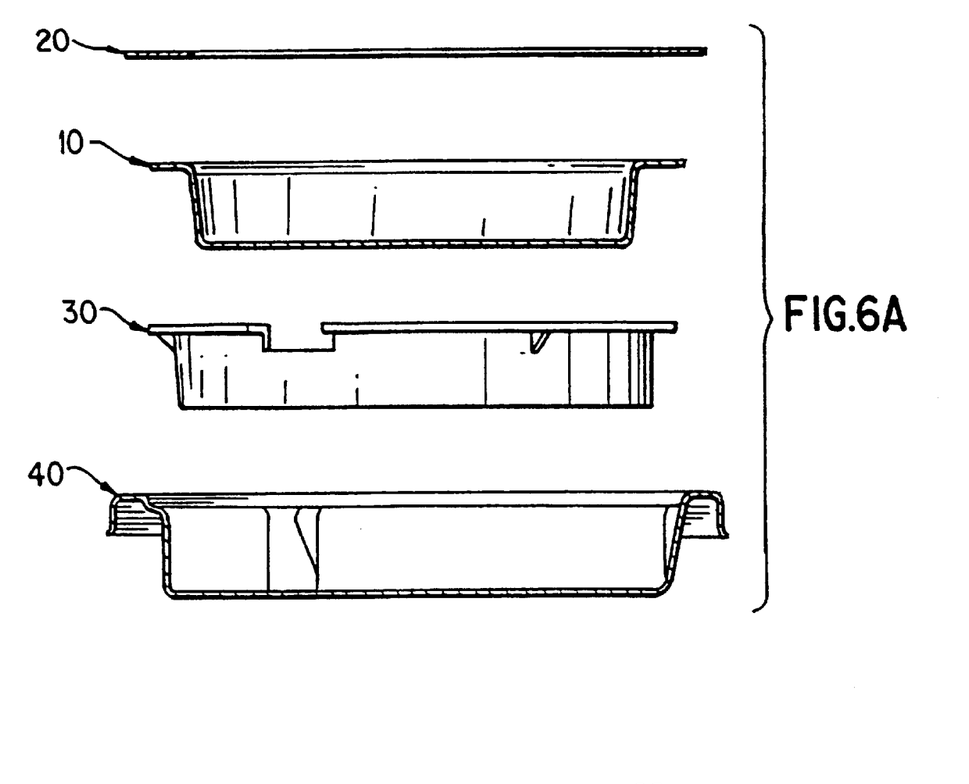
FIGS. 6A and 6B show side views of the assembly, exploded and completed.
Figure 6B:
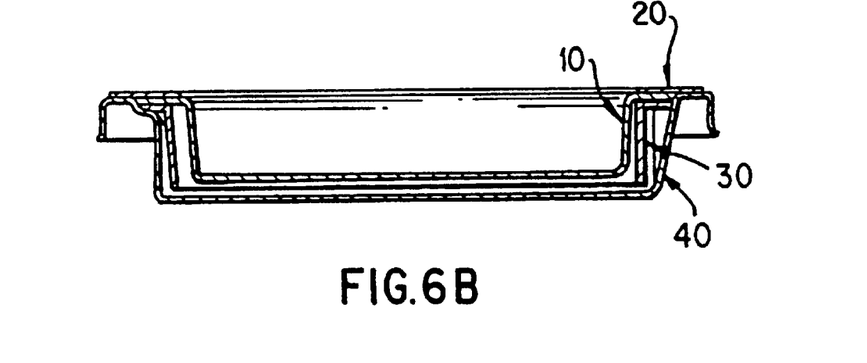

FIGS. 6A and 6B show seal 20; lid 10; carrier 30; and tray 40. Carrier 30 containing a tissue equivalent theron is disposed in tray 40 and is suspended within the tray. Lid 10 with seal 20 is placed over carrier 30 and is suspended over the carrier.

Figure 7:
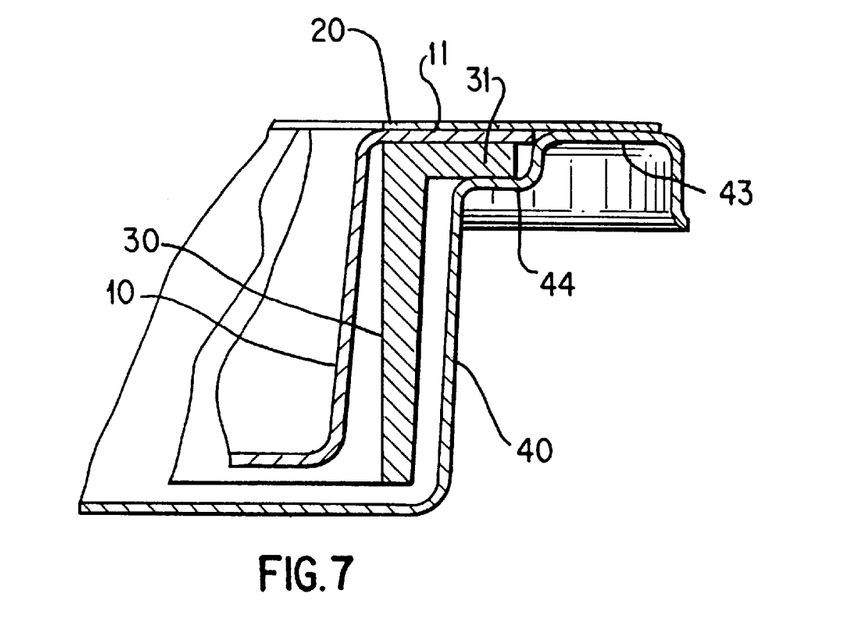
FIG. 7 shows a close view of the assembly.

FIG. 7 shows seal 20; lid flange 11; lid 10; carrier 30; carrier rim 31; carrier supports 44; and tray 40. Carrier 30 containing a tissue equivalent theron is disposed in tray 40 and is suspended within the tray by contact of the bottom surface of carrier rim 31 to the top surfaces of the carrier supports 44. Lid 10 with seal 20 is placed over carrier 30 and is suspended over the carrier by contact of the bottom surface of lid flange 11 to the top surface of carrier rim 31. The top surfaces of both lid flange 11 and tray flange 43 form a planar surface for seal 20.

Figure 8:
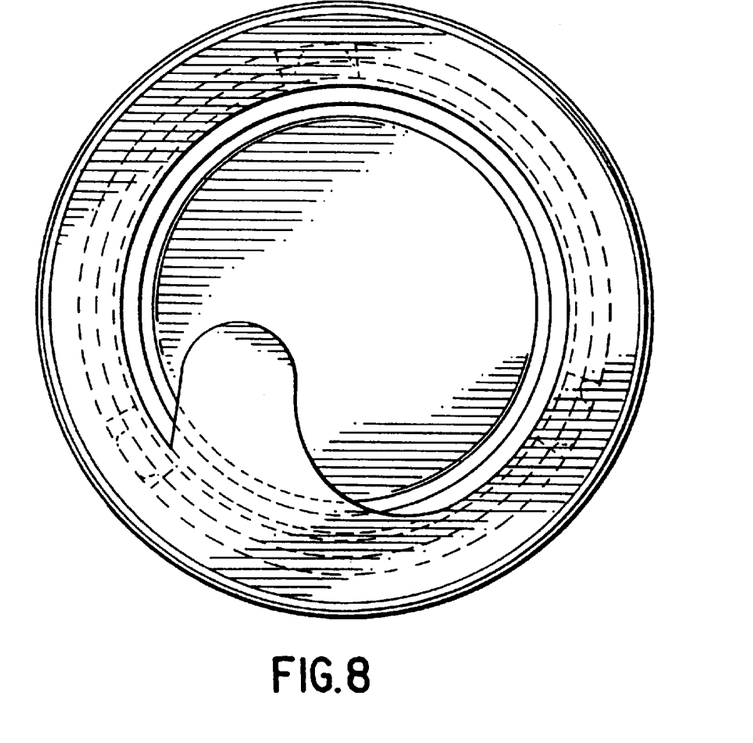
FIG. 8 shows a top view of the assembly, completed.
Figure 9:
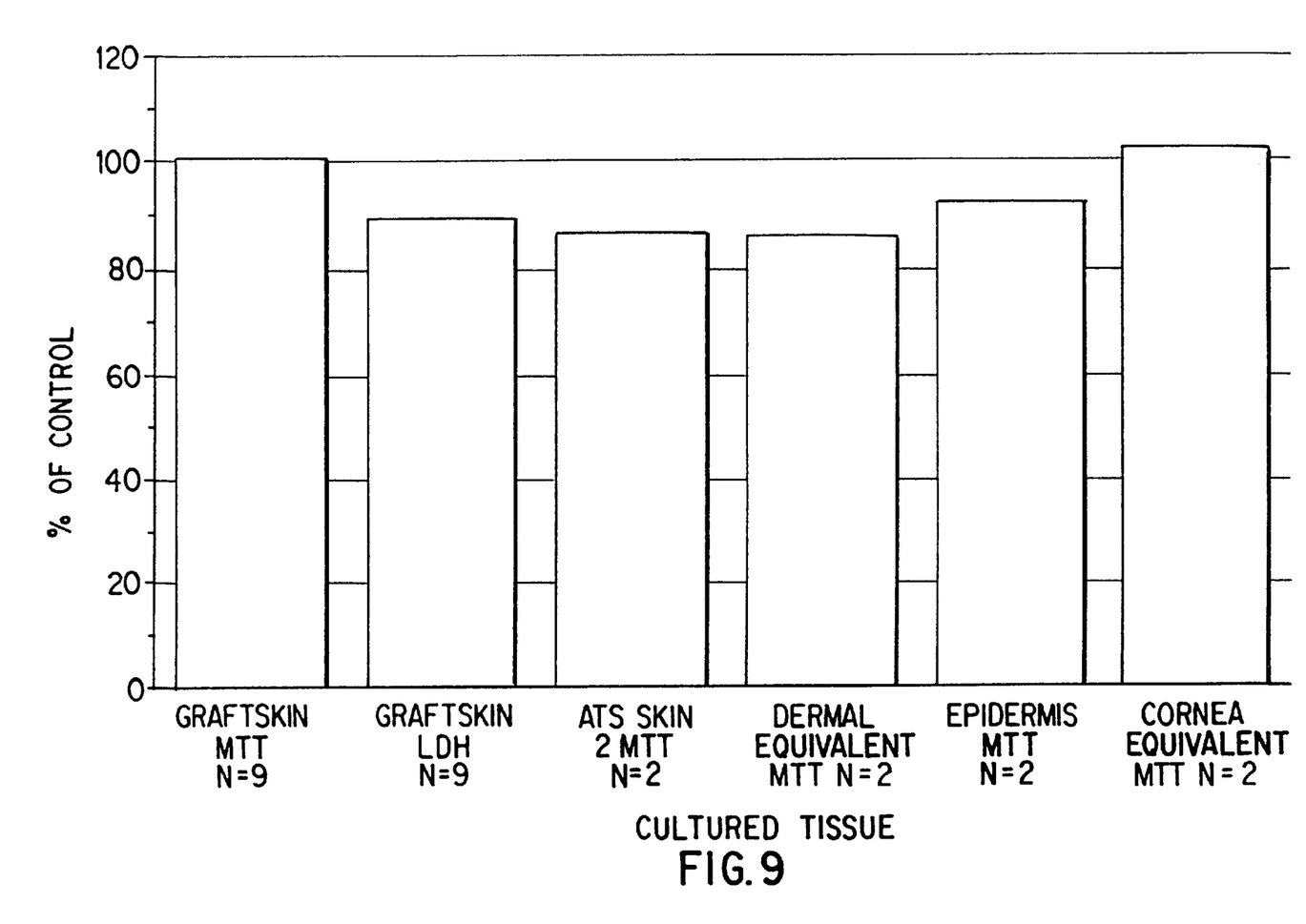
FIG. 9 shows a graph of the viability of cryopreserved cultured tissues compared that of non-cryopreserved cultured tissues. The viability of cryopreserved cultured tissues as measured by MTT is shown. LSE was additionally measured by LDH assay. All cultured tissues are compared to age-matched non-cryopreserved controls and are expressed as a percent of control.

FIG. 8 shows a top view of the assembly.

Materials that trays and lids may be manufactured from are rigid or semiflexible thermoplastic materials that, when heated, are molded by a vacuum or injection molded such as polytetrafluoroethylene (PTFE) or polyethylene terephthalate glycol (PETG). The package trays and lids are preferably sterilized prior use by methods that are known in the art of sterilization. The materials used to fabricate the tray and lid will determine the method of sterilization that can be used. To sterilize PTFE or PETG, Gamma radiation at 2.5 to 3.0 megarads is preferable. Electrical and chemical methods of sterilization known by those skilled in the art, may alternatively be employed.

Cultured tissue equivalents comprise a dermal equivalent of a hydrated collagen lattice contracted by an agent, preferably fibroblasts. In one embodiment, a stratified layer of epidermal cells is cultured on the surface of the dermal equivalent. In another embodiment, the hydrated contracted collagen lattice, contracted by keratocytes, is disposed on a layer of corneal endothelial cells with a stratified layer of corneal epithelial cells cultured on the surface of the lattice. Alternatively, epidermal cells alone may be cultured and induced to stratify to form an epidermal sheet. The cultured tissue equivalent is formed either on a porous membrane of a carrier or on a collagen gel that is adhered to a porous membrane of the bottom surface of a carrier. In addition, other cultured tissue equivalents may be cryopreserved according to the methods of this invention, including, but not limited to, any cultured epidermal sheet, any cultured dermal equivalent, any cultured cornea equivalent, or harvested mammalian skin.

The present invention will now be described using tissue equivalents and the preferred package design as an illustration. It will be understood by those of skill in the art that modifications can be made to the described method and still be within the scope of this invention.

The method of perfusing a tissue equivalent with a cryoprotectant solution is to submerge the tissue equivalent and its attached carrier in a volume of cryoprotectant solution sufficient to submerge the sample and to have equal volume of cryoprotectant solution above and below the tissue equivalent. To a 100 mm petri disk containing the tissue equivalent and carrier is added 25 mL of 2M Glycerol in DMEM for a period of time sufficient to completely perfuse the sample, preferably between one and two hours, but most preferably for about one hour. Extended periods of time in cryoprotectant solution result in reduced cell viability in the tissue, while too short of a time does not ensure complete permeation of cryoprotectant into the tissue. Monolayer constructs will typically require less time for perfusion as they have fewer cell layers and reduced barrier function. During this hour, penetration of cryoprotectant solution is enhanced by agitating the sample and cryoprotectant solution, typically by shaking the petri dish on an orbital platform shaker (Bellco orbital shaker) at 70 rpm in a 10% $CO_2$ gassed chamber. The 10% $CO_2$ environment, the same as the culture environment in which the tissue equivalent was fabricated, prevents the media from degassing, thus maintaining the pH of the base media component of the cryoprotectant. Agitation allows for a faster and a more complete perfusion of cryoprotectant into the tissue equivalent and better reproducibility of results between frozen tissue equivalents. One is able to substitute an orbital shaker with an apparatus that performs an agitative motion in other spatial planes. Additionally, other methods of mechanically enhanced perfusion include, but are not limited to, rocking the construct with cryoprotectant in a vessel on a platform or centrifugation of the construct with cryoprotectant and perfusing cryoprotectant around the construct using a pump.

The carrier and attached tissue equivalent is placed into the tray and a total of about 16.0 ml of cryoprotectant solution is added. The package design allows for equal distribution of cryoprotectant: About 8.0 ml below the carrier and about 8.0 ml on the surface of the tissue equivalent. The lid is then placed onto the tray and the two parts are heat sealed, preferably to the lid stock.

Packaged tissue equivalents are then placed into a programmable freezer (Cryomed or Planer) set at a starting temperature of about room temperature, preferably at 20.0° C. The freezer chamber containing packaged tissue equivalents is cooled at −10.0° C./minute to the solid-liquid phase equilibrium temperature range for the cryoprotectant which is typically, for 2.0M glycerol in DMEM, between about −5.3° C. and −6.0° C. The solid-liquid phase equilibrium temperature is the temperature necessary for seeding ice in the cryoprotectant. The chamber temperature is held for a time for the purpose of equilibrating the internal temperature of the packaged tissue equivalents to the chamber temperature. The cooling rate used to obtain the seeding temperature is not critical. A hold time of about 40 minutes is sufficient to ensure thermal equilibration but the time will vary depending on chamber size, air circulation within the chamber, and number of packages to be frozen. While at least 30 minutes is typically needed, up to one hour can be taken to ensure equilibration. After the hold time, extracellular ice formation by seeding is initiated.

Ice seeding is defined as a method of initiating ice formation in the extracellular cryoprotectant. One preferred method of ice seeding is by contacting the side of the tray containing the tissue with a chilled probe. such as a liquid nitrogen chilled (−196° C.) steel rod. The contact site of the rod to the package must be below the level of the cryoprotectant freeze media in the package. Another preferred method is to directly release an expanding gasses such as freon or $CO_2$ to the outside of the package. Ice formation can be initiated by a chamber spike where the temperature of the chamber is lowered and raised within a range sufficient to form an ice crystal. Other methods of ice seeding known in the art may be substituted.

After all tissue equivalents are seeded with ice crystals, the units are held an additional one hour to allow for thermodynamic equilibration and propagation of the ice seed crystal throughout the cryoprotectant. Cooling is then resumed at a rate of preferably between about −0.02 to about −0.3° C.; more preferably between about −0.05 to about −0.1° C./minute; and most preferably at about −0.07° C./minute to a final temperature preferably at least or below −70.0° C.; more preferably at −120° C.; even more preferably at −140° C.; or most preferably at −196° C. As the final freezing temperature approaches the glass transition temperature of water, −120° C., the less likely there will be detrimental temperature fluctuations during transfers to final storage locations.

Cryopreserved tissue equivalents are transferred from the programmable freezer to storage in a vapor phase liquid nitrogen storage tank (Dewar) at a temperature between about −120° to −150° C., or in liquid nitrogen at −196° C. until use.

To thaw, cryopreserved cultured tissue equivalents are removed from vapor phase liquid nitrogen storage and transferred to dry ice to warm to about −75° C. Once equilibrated at −75° C., cultured tissue equivalents are then transferred to an environment, preferably a waterbath, preferably set at 37° C.; or more preferably set at 4° C.; or most preferably set at room temperature. Once it is visible that all the cryoprotectant medium is turned to liquid phase, the cultured tissue equivalent package units are preferably transferred to a biological safety cabinet, or other aseptic area and sanitized with ethanol. The lid of the dishes are removed by peeling or cutting the lid stock from the bottom of the unit. The carriers containing cultured tissue equivalents are then each transferred to petri dishes while pouring off excess cryoprotectant. To rinse the cultured tissue equivalent of residual cryoprotectant, 25 mL of rinse solution, preferably DMEM at room temperature, is then added to the petri dish containing the cultured tissue equivalent for about 30 minutes. Other sufficient rinse agents, preferably physiological strength solutions, such as cell culture media or phosphate buffered saline, may be determined by the skilled artisan. The rinse solution is exchanged a second time for an additional 30 minutes. Rinse times may vary depending on the complexity of the tissue.

The cultured tissue equivalent unit may be then transferred back to its original culture dish and recultured in culture maintenance medium at 37° C./10% $CO_2$. Alternatively, the equivalent may be applied to a patient or tested for a response to contact with a substance as described in U.S. Pat. No. 4,835,102.

The following examples are provided to better elucidate the practice of the present invention and should not be interpreted in any way to limit the scope of the present invention. Those skilled in the art will recognize that various modifications can be made to the methods described herein while not departing from the spirit and scope of the present invention.

EXAMPLES

Examples 1 to 3

Examples 1 to 3 show the cryopreservation and thawing techniques of this invention with the preferred package design.

Example 1

Cryopreservation of Living Skin Equivalent (LSE) With the Package Design

Living Skin Equivalent (LSE) constructs were prepared in accordance to U.S. Ser. No. 08/193,809. LSEs and attached 75 mm carrier inserts (TRANSWELL®, Costar, Cambridge), at 9 to 10 days post air lift, were placed in 100 mm petri dishes (Costar). LSE constructs were perfused with cryoprotectant by submerging the constructs and the transwell with 25 mL of cryoprotective media, 2M Glycerol in DMEM, in the 100 mm petri dish for one hour. During perfusion, the constructs were agitated for one hour on an orbital shaker (Bellco) at 70 rpm in a 10% $CO_2$ gassed chamber. Agitation allows for more complete perfusion and better reproducibility of the cryopreservation method. After LSE were perfused, the petri dishes containing LSE, carrier inserts and extracellular freezing media (2M Glycerol and DMEM) were placed in a cryopreservation package and heat sealed. Cryopreservation packages are described in co-pending patent application, U.S. Ser. No. 08/593,587, filed the same day as this application.

The chamber of a programmable freezer (Planar) was outfitted with the invention described herein. The freezer was set at a starting temperature of 20.0° C. The tubing lines were purged with freon for a single one second interval to remove any air in the lines. Packaged LSE units were placed securely into racks accommodating eight LSE units each. The racks, guided by locating pins, were placed adjacent to the spray rails. The chamber door of the freezer was closed to seal the chamber from the external environment.

LSE units were cooled at −10° C./minute to −6° C. and the chamber temperature was held at −6° C. for 40 minutes to equilibrate the cryoprotectant and perfused constructs to the chamber temperature. After the 40 minute hold, extracellular ice was initiated by directly discharging freon for one second at close proximity to the side of the package. The freon, as it evaporated from the surface of the package, caused the contact area of the freon to drop in temperature enough to initiate extracellular ice formation.

After all LSE units were seeded with ice crystals, the units are allowed to equilibrate for one hour at −6° C. The chamber temperature was then cooled at −0.07° C./minute to a final temperature of −20° C. The chamber was then cooled at −0.5° C./min to a final temperature of −70° C. Once the LSE units were cryopreserved, they were transferred to a vapor phase storage tank (Dewar) at a temperature of −120° to −150° C.

Example 2

Thawing Cryopreserved LSE

Cryopreserved LSE were removed from vapor phase liguid nitrogen storage and transferred to dry ice to warm to about −75° C. Once equilibrated at −75° C., cultured tissue equivalent are then transferred to a waterbath preferably set at 37° C.; or more preferably set at 4° C.; or most preferably set at room temperature. Once it is visible that all the cryoprotecant medium is turned to liquid phase, the cultured tissue equivalent package units are prefeably transferred to a biological safety cabinet, or other aseptic area and sanitized with ethanol. The lid of the dishes are removed by peeling or cutting the lid stock from the bottom of the unit. The carriers containing cultured tissue equivalents are then each transferred to petri dishes while pouring off excess cryoprotectant. To rinse the cultured tissue equivalent of residual cryoprotectant, 25 mL of (room temp) rinse solution, preferably DMEM is then added to the petri dish containing the cultured tissue equivalent for about 30 minutes. Other sufficient physiological rinse solutions, such as other cell culture media or phosphate buffered saline, may be determined by the skilled artisan. The rinse solution is exchanged a second time for an additional 30 minutes.

Thawed cryopreserved and control samples were processed by histological methods and evaluated by light microscopy for morpohological organization and viability and showed near 100% viablility and were almost indistinguishable from control.

Example 3

Evaluation of the Cryopreservation Package Design for Warming Rate and Thermal Uniformity A cryopreservation package of the present invention was evaluated for uniform heat transfer. To a carrier membrane, without a cultured tissue equivalent, were mounted five thermocouples, one in the center and four equally spaced 1.0 mm from the peripheral wall of the carrier. Thermocouple leads exited the package from the side between lid and tray flanges to an temperature recorder (Azonix Scanner Plus). The package was filled with 17 mL of cryoprotectant and the package was heat sealed. The package was equilibrated to −70° C. and then transferred to a water bath set at 20° C. The temperature recorder recorded the temperature at each thermocouple every 1 to 2 seconds during warming. The package warmed at a rate of 700° C./min. initially and slowed down as it approached the melting point of the cryoprotectant solution The thermal uniformity was between 2° C. and 6° C. of the average thermocouple temperature during the fastest warming rates and approached 8° C. as it reached the melting point of the solution.

Examples 4 to 12 show the cryopreservation method of this invention on different tissues.

Example 4

Cryopreservation of Epidermal Sheets

Epidermal sheets were procured from mature LSE at 12 days post air-lift. Removal of the epidermal sheet was accomplished by peeling the dermal substrate layer from the epidermal layer with forceps and discarding the dermal layer. Each sheet was cut in to three equivalent pieces. One piece from each sheet was fixed as a control. The remaining two pieces form each sheet were placed on top of a 75 mm polycarbonate transwell membrane (Costar) in 100 mm culture dishes (Costar). Each piece was perfused with 25 mL of DMEM and 2 Molar Glycerol for one hour. The dishes containing constructs were placed on an orbital shaker (Bellco) at 70 rpm for one hour in a 10% $CO_2$ gassed chamber. After the epidermal sheet was perfused, the petri dish containing epidermal sheet, transwell and extracellular freezing media (2M Glycerol and DMEM) were placed in a bag and vacuum sealed (Audiovox) programmed for a 5 second vacuum and a 3.9 second seal time.

Packaged epidermal sheets were placed into the programmable freezer (Planer) at a starting temperature of 20.0° C. Epidermal sheets were cooled at −10.0° C./minute to −6.0° C. The temperature was allowed to hold for 20 minutes at −6.0° C. to equilibrate to chamber temperature. After the 20 minutes hold, extracellular ice was initiated by contact of the outside of the bag, below the level of the freeze media, with a liquid nitrogen chilled probe. After all epidermal sheets had been seeded with ice crystals, the temperature was held an additional 5 minutes at −6.0° C. The chamber was then cooled at −1.0° C./minute to −8.0° C. The temperature was then allowed to hold for 30 minutes at −8.0° C. to allow for uniform distribution of ice throughout the sample. The chamber was then cooled at −0.1° C./minute to a final temperature of −70.0° C.

Cryopreserved epidermal sheets were removed from the freezer and the bags were cut from the petri dishes and the lids removed. To thaw, 40 mL of warmed (37° C.) DMEM was aseptically poured into each petri dish. After 45 seconds, all liquid was removed from the dishes and an additional 40 mL aliquot was added to each dish for two minutes After all ice was thawed, epidermal sheets were rinsed with 25 mL of DMEM for 30 minutes. The media was exchanged a second time for an additional 30 minutes. The epidermal sheets were then incubated in culture maintenance medium at 37° C./10% CO2 for 24 hours prior to analysis. The incubation time was allowed for the lag typically seen for frozen cells to reestablish steady state conditions. Again, the incubation time was allowed for the lag typically seen for frozen cells to reestablish steady state conditions.

Of the two remaining pieces from each epidermal sheet, one from each was processed for histology and one piece from each sheet was assayed following the MTT assay protocol. Comparing photomicrographs of non-cryopreserved epidermal sheet and cryopreserved epidermal sheet of Example 4 showed that the three basic features of the epidermis: the basal layer of the epidermis, the suprabasal layers of the epidermis and the stratum corneum of the epidermis were all preserved by this method. All layers were intact and the overall morphology of the cryopreserved epidermal sheet was identical to that of the non-cryopreserved epidermal sheet.

Example 5

Cryopreservation of Dermal Equivalent

Dermal equivalents used in this study were the non-epidermalized component of the LSE. Dermal equivalents were frozen at 8 days post cast. The dermal equivalents were perfused with cryoprotectant by submerging the dermal equivalents attached to 75 mm transwell (Costar) placed in 100 mm petri dishes (Costar) with 25 mL of DMEM and 2 Molar Glycerol for one hour. The petri dishes were placed on an orbital shaker (Bellco) at 70 rpm for one hour in a 10% CO2 gassed chamber. After dermal equivalents were perfused, the petri dishes, dermal equivalents, transwells and extracellular freezing media were placed into the programmable freezer (Planer) at a starting temperature of 20.0° C. The chamber was then cooled at −10.0° C./minute to −6.0° C. The temperature was held for 20 minutes to equilibrate to chamber temperature. After the 20 minutes hold, extracellular ice was initiated by contact of the outside of the dishes, below the level of the freeze media, with a liquid nitrogen chilled probe. After all dermal equivalents had been seeded with ice crystals, the temperature was held an additional 5 minutes at −6.0° C. The chamber was then cooled at −1.0° C./minute to −8.0° C. The chamber temperature was held again for 30 minutes at −8.0° C. to allow for uniform distribution of ice throughout the sample. Dermal equivalents units were then cooled at −0.1° C./minute to a final temperature of −70.0° C.

Cryopreserved dermal equivalents were then removed from the freezer and the lid of the dish was removed. To thaw, 40 mL of warmed (37° C.) DMEM was aseptically poured into each petri dish. After 45 seconds, all liquid was removed from the dishes and an additional 40 mL aliquot was added to the dishes for two minutes After all ice was thawed, dermal equivalents were rinsed with 25 mL of DMEM for 30 minutes The media was exchanged a second time for an additional 30 minutes The dermal equivalents, still attached to the transwells, were then transferred back to the culture dishes and incubated in culture maintenance medium at 37° C./10% $CO_2$ for 24 hours prior to analysis. The incubation time was allowed for the lag typically seen for frozen cells to reestablish steady state conditions. Samples were assayed using the MTT assay protocol.

Example 6

Cryopreservation of Cornea Equivalents

Cornea equivalents, attached to 24 mm culture transwells (Costar), 9 days post moist air lift, were placed into six well cluster dishes (Costar). The method of perfusing cornea equivalents with cryoprotectant was to submerge each cornea equivalent and transwell with 4 mL extracellular freezing media (2M glycerol in DMEM) in the six well cluster dishes for one hour. The six well cluster dishes containing the cornea constructs were shaken for one hour on an orbital shaker (Bellco) at 70 rpm in a 10% $CO_2$ gassed chamber. After cornea equivalents were perfused, the petri dishes containing cornea equivalents, transwells and extracellular freezing media were placed into the programmable freezer (Planer) at a starting temperature of 20.0° C. Cornea equivalents were cooled at −10.0° C./minute to −6.0° C. The temperature was held for 20 minutes to equilibrate to chamber temperature. After the 20 minutes hold, extracellular ice was initiated by contact of the outside of each well in the cluster plate, below the level of the freeze media, with a liquid nitrogen chilled probe. After all cornea equivalents had been seeded with ice crystals the temperature was held an additional 5 minutes at −6.0° C. prior to cooling at −1.0° C./minute to −8.0° C. The temperature was held again for 30 minutes at −8.0° C. to allow for uniform distribution of ice throughout the sample. Cornea equivalent units were cooled at −0.1° C./minute to a final temperature of −70.0° C.

Cryopreserved cornea equivalents were removed from the freezer. The lid of the dish was removed. To thaw, 6 mL of warmed (37° C.) DMEM was aseptically poured into each well of the cluster plate. After 45 seconds, all liquid was removed from the dish and an additional 6 mL aliquot was added to the dish for two minutes Using sterile forceps the cornea equivalents and attached transwells was transferred to a new cluster dish. To rinse, 4 mL of DMEM was added to each well for 30 minutes. The media was exchanged a second time for an additional 30 minutes The cornea units were then transferred back to the/same culture dish and incubated in cornea maintenance medium at 37° C./10% $CO_2$ for 24 hours prior to analysis. The incubation time was allowed for the lag typically seen for frozen cells to reestablish steady state conditions. Samples were assayed using the MTT assay protocol.

Example 7

Cryopreservation of Harvested Murine Skin

Wild type mice, strain B6CB6YF1, were euthanized by Nembutal overdose. The skin was harvested aseptically. Excess blood vessels, fat and connective tissue were removed from the dermis. Murine skin was trimmed to a rectangular 1 cm×2 cm piece. Murine skin pieces were then placed on a 75 mm transwell (Costar) in 100 mm petri dishes (Costar). Murine skin was perfused with cryoprotectant by submerging in 25 mL of 2M Glycerol in DMEM in the 100 mm petri dishes for one hour. During perfusion, the petri dishes each containing the murine skin and the transwell were shaken for one hour on an orbital shaker (Bellco) at 70 rpm in a 10% CO2 gassed chamber. Control, non-cryopreserved mouse skin was kept in nutrient media at 4° C. for the duration of the cryopreservation and thawing process (2 days) before skin grafting.

After murine skin is perfused, the petri dishes containing murine skin, transwells and extracellular freezing media are placed into the Planer programmable freezer at a starting temperature of 20.0° C. Murine skin was cooled at −10.0° C./minute to −6.0° C. and were allowed to hold at −6.0° C. for 20 minutes to equilibrate to chamber temperature. After the 20 minute hold, extracellular ice was initiated by contact of the outside of the dish with a liquid nitrogen chilled probe. The contact site must be below the level of the freeze media. After all murine skin had been seeded with ice crystals, the temperature was held an additional 5 minutes at −6.0° C. prior to cooling at −1.0° C./minute to −8.0° C. The temperature was held again for 30 minutes at −8.0° C. to allow for uniform distribution of ice throughout the sample. The units were then cooled at −0.1° C./minute to a final temperature of −70.0° C.

Cryopreserved murine skin was removed from the freezer and the lid of the dish was removed. To thaw, 40 mL of warmed (37° C.) DMEM was aseptically poured into the petri dishes. After 45 seconds, all liquid was removed from the dishes and an additional 40 mL aliquot was added to the dishes for two minutes After all ice was thawed, murine skin was rinsed in the dishes with 25 mL DMEM for 30 minutes The media was exchanged a second time for an additional 30 minutes.

Thawed cryopreserved and control samples were processed for histology or were grafted to mice. The photomicrographs of non-cryopreserved mouse skin compared with cryopreserved mouse skin showed that the four basic features of mouse skin, the dermis with fibroblasts, the basal layer of the epidermis, the suprabasal layers of the epidermis and the stratum corneum of the epidermis were preserved by this method. All layers were intact and the overall morphology of cryopreserved mouse skin was identical to that of non-cryopreserved mouse skin.

Example 8

Cryopreservation of ATS SKIN2™

SKIN2™, model ZK 1300 (Advanced Tissue Sciences, La Jolla, Calif.), was removed from the packaging according to shipping inserts upon arrival and were placed in culture dishes (Costar). Transwell inserts were placed above the SKIN2™ to keep the skin construct submerged. SKIN2™ was perfused with cryoprotectant by submerging SKIN2™ in 2M Glycerol in DMEM in the culture dishes for one hour. During perfusion, the culture dishes containing the construct and the transwell were shaken for one hour on an orbital shaker (Bellco) at 70 rpm in a 10% $CO_2$ gassed chamber.

After SKIN2™ is perfused, the units were placed into the programmable freezer (Planar) at a starting temperature of 20.0° C. SKIN2™ units were cooled at −10.0° C./minute to −6.0° C. and were allowed to hold at −6.0° C. for 20 minutes to equilibrate to the chamber temperature. After the 20 minute hold, extracellular ice was initiated by contact of the outside of the dishes below the level of the freeze media with a liquid nitrogen chilled probe. After all SKIN2™ units were seeded with ice crystals, the temperature was held for an additional 5 minutes at −6.0° C. The chamber temperature was then cooled at −1.0° C./minute to −8.0° C. SKIN2™ units were allowed to hold for 30 minutes at −8.0° C. to allow for uniform distribution of ice throughout the sample. SKIN2™ units were then cooled at −0.1° C./minute to a final temperature of −70.0° C.

Cryopreserved SKIN2™ were removed from the freezer, the lids of the dishes was removed and warmed (37° C.) DMEM was aseptically poured into each culture dish. After 45 seconds, all liquid was removed from the dishes and another addition of DMEM was added to each dish for two minutes. Once thawed, the SKIN2™ unit and attached transwell were transferred to a new culture dishes, using sterile forceps. To rinse the SKIN2™ of cryoprotectant, DMEM was added to each culture dish containing the SKIN2™ for 30 minutes. The media was exchanged a second time for an additional 30 minutes. The SKIN2™ unit was then transferred back to the same type culture dish and was incubated in culture maintenance medium at 37° C./10% CO2 for 24 hours prior to analysis. Again, the incubation time was allowed for the lag typically seen for frozen cells to reestablish steady state conditions.

Cryopreserved and control constructs were assayed following the MTT assay protocol for SKIN2™ model ZK1300, enclosed with the product, and also by histological evaluation. The photomicrographs of non-cryopreserved SKIN2™ compred with cryopreserved SKIN2™ showed that the four basic features of SKIN2™, the collagen lattice with fibroblasts, the basal layer of the epidermis, the suprabasal layers of the epidermis and the stratum corneum of the epidermis were all preserved by this method. All layers were intact and the overall morphology of cryopreserved SKIN2™ was similar to that of non-cryopreserved SKIN2™.

Example 9

Metabolic Mitochondrial Activity Assay (MTT)

Frozen and non-frozen (control) LSE, epidermal sheet, dermal equivalents and corneal equivalents were tested using the MTT assay. [SKIN2™ constructs were assayed according to "MTT Assay Protocol for use with Model ZK1300", enclosed with the shipping inserts.] Cell viability of the constructs were measured using the MTT assay, a calorimetric MTT conversion assay developed to measure cellular growth and viability. This assay is described in detail in Gay et al., "The Living Skin Equivalent as a Model In Vitro for Ranking the Toxic Potential of Dermal Irritants," Toxic. in Vitro, 6:303–315 (1992). The metabolic reduction of the soluble tetrazolium salt to a blue formazan precipitate is dependent on the presence of viable cells with intact mitochondrial function. This assay is used to quantitate cytotoxicity in a variety of cell types, including cultured human keratinocytes.

To the culture dishes containing LSE, epidermal sheet and dermal equivalent, 40 mL of assay medium and to the wells containing corneal equivalents, 1.5 mL of assay medium containing 0.33 mg/mL MTT (Sigma Chemical Co., St. Louis, Mo.) was added. The tissue equivalents were incubated in the MTT assay medium for 3–4 hours. At the end of the conversion period, the tissue equivalent was biopsied using an 8-mm diameter skin biopsy punch. The punch biopsies were then extracted for 2–3 hours at room temperature in 0.3 mL isopropanol, acidified with 0.04N HCl. At the end of the extraction period, 0.2 mL of each extract was transferred to a well of a 96-well plate. The absorbencies were read on a plate reader (Dynatech) at 570 nm with the isopropanol extraction medium as a blank. MTT values obtained from thawed cryopreserved samples were compared to corresponding control samples and expressed in terms of percent of control (FIG. 4).

Example 10

Lactose Dehydrogenase Assay (LDH)

LDH is an enzyme typically found in a viable cell. Damage to the cell causes a release of the enzyme and a corresponding decrease in the enzyme activity detected by this assay.

Thawed cryopreserved and control samples of LSE were punched with an 8 mm diameter skin biopsy punch. Three samples were taken from each LSE unit. Punch samples were placed in a 15 mm tubes with 1 mL of 0.1M triethanolamine buffer (on ice) and homogenized with an electric tissue homogenizer for one minute. The samples were then centrifuged at 1000 g at 4.0° C. The supernatant was then assayed. LDH cocktail reagent was prepared by mixing together the following: 3.00 mL phosphate buffer (0.1 mol/l; pH 7.0), 0.1 mL pyruvate, Na salt (2.5 mg/mL), and 0.05 mL NADH, Na salt (10 mg/mL). 100 $\mu$L of sample supernatant was added to 900 $\mu$L of the reagents and allowed to react for two minutes. The change in absorbance over the two minutes was recorded. The average of three samples per cryopreserved LSE unit were compared to the non-frozen controls. Sample values were compared to corresponding control values and expressed in terms of percent of control (FIG. 4).

Example 11

Bioequivalence of Cryopreserved LSE To Non-Cryopreserved LSE

To demonstrate the bioequivalence of cryopreserved and non-cryopreserved LSE, a grafting study to athymic mice was performed.

LSE units, cryopreserved according to the method outlined in Example 1, were thawed one day before grafting and recovered in maintenance media for twenty-four hours.

Four experiments were performed in which a total of 66 athymic mice of the strain B6CB6YF1/J-nu (Jackson Harbor Labs) were grafted with either cryopreserved LSE (n=43) or non-cryopreserved (control) LSE (n=23). Animals were anesthetized with Nembutal. A 2×2 cm full thickness skin section was excised from the dorsum of each mouse, sparing the panicculus carnosus. LSE grafts, either control or cryopreserved, were placed on the wound and trimmed to fit. All grafts were dressed with one layer of petrolatum impregnated gauze (vendor) and covered by two adhesive bandages (vendor). The dressings were removed at 7 days post-graft.

At 14 days post-graft, all animals were euthanized and photographed. The graft site was then excised for histological analysis and evaluation. The gross photographs and micrographs showed no difference in graft integration between control LSE or thawed, cryopreserved LSE. No significant difference was seen in rates of wound contracture between control or cryopreserved grafts.

Example 12

Syngenaic Skin Grafting of Cryopreserved and Control Mouse Skin

To demonstrate the bioequivalence of cryopreserved and non-cryopreserved mouse skin, a syngenaic skin grafting study was performed.

Wild type mice, strain B6CB6YF1, were euthanized by Nembutal overdose. The skin was harvested aseptically. Excess blood vessels, fat and connective tissue were removed from the dermis in preparation for skin grafting. Mouse skin was cryopreserved and thawed following the method in Example 7, Control, non-cryopreserved mouse skin was kept in a nutrient media at 4° C. for the duration of the cryopreservation and thawing process, a total of two days, before skin grafting.

Six mice of the same strain received skin grafts, two received control, non-cryopreserved mouse skin and four received thawed, cryopreserved mouse skin. The mice were anesthetized with Nembutal. A 2×2 cm full thickness skin section was excised from the dorsum of each mouse, sparing the panicculus carnosus. Mouse skin grafts, either control or cryopreserved, were placed on the wounds and trimmed to fit. All grafts were dressed with one layer of petrolatum impregnated gauze, covered by two adhesive bandages. These dressings were removed at 7 days post-graft.

At thirty days post-graft, all animals were euthanized and photographed. The graft site was then excised for histological analysis and evaluation. The gross photographs and micrographs showed that there was no difference in graft integration between control mouse skin or thawed, cryopreserved mouse skin. No significant difference was seen in rates of wound contracture between control or cryopreserved grafts.

Although the foregoing invention has been described in some detail by way of illustration and example for purposes of clarity of understanding, it will be obvious to one skilled in the art that certain changes and modifications may be practiced within the scope of the appended claims.

What we claim is:

1. An apparatus for holding biological material comprising:
   a tray having a bottom wall, a sidewall, a flange with a horizontal portion, and at least one support between the flange and the sidewall;
   a carrier having a sidewall, a membrane across a lower end of the sidewall, and a rim at an upper end of the sidewall, the rim resting on the support of the tray when the carrier is positioned in the tray; and
   a lid having a peripheral portion for resting on the rim of the carrier so that the peripheral portion of the lid is on the rim and coplanar with the horizontal portion of the flange of the tray.

2. The apparatus of claim 1, wherein the lid has a bottom wall, a sidewall, and a flange, the flange including the peripheral portion.

3. The apparatus of claim 1, further comprising a seal connected to the flange of the lid and to the flange of the tray.

4. The apparatus of claim 3, wherein the seal is held to the flanges with adhesive.

5. The apparatus of claim 3, wherein the seal is heat sealed to the flanges.

6. The apparatus of claim 1, wherein the tray is a monolithic body.

7. The apparatus of claim 1, wherein the lid is a monolithic body.

8. The apparatus of claim 1, further comprising a biological material on the membrane and a cryoprotectant in the tray.

9. The apparatus of claim 1, wherein the support includes a step in the sidewall, monolithic with the sidewall and the flange of the tray.

10. The apparatus of claim 1, further comprising a seal connected to the flange of the lid and to the flange of the tray, wherein the lid has a bottom wall, a sidewall, and a flange including the peripheral portion, wherein the tray is a monolithic body, and wherein the lid is a monolithic body.

11. An apparatus comprising:
    a tray having a bottom wall, a sidewall, and a flange;
    a carrier having a sidewall, a membrane attached to a lower end of the sidewall, and a rim at an upper end of the sidewall, the carrier resting in the tray so that the membrane is spaced above the bottom wall of the tray;
    a lid over the carrier;
    a biological material in the carrier and on the membrane; and
    a cryoprotectant solution in the tray and the carrier such that a vertical distance between the biological material to the lid is equal to a vertical distance from the biological material to the bottom wall of the tray.

12. The apparatus of claim 11, wherein the biological material is a tissue equivalent.

13. The apparatus of claim 11, wherein the lid has a bottom wall, a sidewall, and a flange, the bottom wall of the lid being parallel to the membrane and to the bottom wall of the tray.

14. The apparatus of claim 11, wherein the lid has a peripheral portion that rests on the rim of the carrier and that is coplanar to a horizontal portion of the flange of the tray.

15. The apparatus of claim 14, further comprising a seal on and sealed to the flanges of the lid and the tray without contacting the rim.

16. An apparatus for holding biological material comprising:
    a tray having a bottom wall, a sidewall, and a flange;
    a carrier for holding the biological material and having a sidewall and a rim extending from the sidewall, the carrier supported in the tray;
    a lid having a peripheral portion for resting on the rim of the carrier; and
    a seal over the lid and sealed to the peripheral portion of the lid and the flange of the tray, but not in contact with the carrier.

17. The apparatus of claim 16, wherein the seal is sealed to the flanges with an adhesive.

18. The apparatus of claim 16, wherein the seal is heat sealed to the flanges.

19. The apparatus of claim 16, wherein the tray and lid are monolithic bodies.

20. The apparatus of claim 19, wherein the tray has a monolithic step between the sidewall and flange on which the rim of the carrier rests, the location of the carrier and thickness of the rim causing the peripheral portion to be coplanar with a horizontal portion of the flange.

* * * * *